United States Patent [19]

Grandjacques et al.

[11] Patent Number: 4,487,503
[45] Date of Patent: Dec. 11, 1984

[54] REFRACTOMETER USING THE LIMITING ANGLE METHOD

[75] Inventors: Benoît Grandjacques, Maisons Alfort; Jacques Moirez, Paris; Michel Saint-Sevin, Gagny; Michel Blot, Arpajon; Jean-Michel Baluteau, Livry Gargan, all of France

[73] Assignee: Sopelem, Levallois-Perret, France

[21] Appl. No.: 318,905

[22] Filed: Nov. 6, 1981

[30] Foreign Application Priority Data

Nov. 14, 1980 [FR] France ............... 80 24244

[51] Int. Cl.³ .......................................... G01N 21/43
[52] U.S. Cl. ................................................. 356/136
[58] Field of Search ............... 356/128, 135, 136, 137

[56] References Cited
U.S. PATENT DOCUMENTS 2,807,976 10/1957 Vossberg ............................ 356/136
3,487,069 12/1969 Maselli ................................ 356/135
3,650,631 3/1972 Grässel et al. ...................... 356/136

FOREIGN PATENT DOCUMENTS 2222642 11/1973 Fed. Rep. of Germany ...... 356/135
623143 8/1978 U.S.S.R. .............................. 356/136

Primary Examiner—R. A. Rosenberger
Attorney, Agent, or Firm—Pollock, Vande Sande & Priddy

[57] ABSTRACT

Refractometer for measuring the refractive index of a medium (2), using the limiting angle method. A source (4) illuminates a source slit (5) which has as its image with respect to an optical system (S) one of the parallel and regularly spaced slits (5') of a grille (6) fixed perpendicular to the optical axis each of the slits (5') corresponding to an angle of incidence of the optical beam on a prism (3). Turning of a rhombohedron causes the image (5') of the source slit (5) on the grille (6) to be successively on each of the slits (5') of the grille (6). The pupil ($L_1$), located in the plane of the source, is conjugate with the exit face (8) of the prism (3) and remains stationary when the image (5') of the source slit (5) is moved over the grille (6).

7 Claims, 3 Drawing Figures

REFRACTOMETER USING THE LIMITING ANGLE METHOD

BACKGROUND OF THE INVENTION

The invention concerns a refractometer using the limited angle method.

Refractometers using the limiting angle method have been used for a long time to measure the refractive index of a medium, particularly a liquid medium: a prism of known index is placed in contact with the medium the index of which is to be measured and the interface of these two media is illuminated with the aim of determining the minimum angle of incidence at which reflection is total, i.e., the limiting angle.

To determine the limiting angle, the surface separating the two media can, for example, be illuminated from all directions of incidence simultaneously, and by, for example, moving a small cell in front of the reflected beam, the angle of incidence can be determined at which the amount of light received by the cell varies rapidly. A large cell receiving the whole of the beam reflected at once can also be used, and on the image received by this cell the position of the separator can be determined.

Also, instead of illuminating the surface separating the two media from all directions of incidence simultaneously, a small pencil can be selected corresponding to one direction of incidence, and the position of this pencil can be made to vary. This pencil can be selected by means of a movable slit positioned in the pupil of the objective. A fixed cell with large enough dimensions to be reached successively by each of the beams reflected determines the position of the slit at which the illuminance of the cell varies rapidly.

These procedures, however, have certain disadvantages.

In particular, since the lamp either must illuminate from all directions of incidence simultaneously or must illuminate a slit which is movable in a beam, it is necessary to choose a lamp which is powerful enough and therefore with a relatively limited life.

In addition, the two procedures already described assume that the light source is very precisely positioned and that there is a directionally homogeneous distribution of illuminance. As a result, if the lamp must be changed relatively often, it will be difficult to position the new lamp in exactly the same position as the first.

In addition, movement of the cell or the slit is expensive and entails inaccuracies.

In the procedure in which there is illumination from all directions of incidence simultaneously, considerable diffusion and hence stray light is also present.

The procedures known to date are consequently relatively expensive and inaccurate, and the invention attempts to solve these problems.

SUMMARY OF THE INVENTION

The invention concerns a refractometer for measuring the refractive index of a medium, using the method of the limiting angle of total reflection, comprising a reference prism, with known refractive index, which can be put in contact with the medium to be observed, a light source, an objective for focusing light rays from the source onto the prism, a photoelectric measuring cell located at the exit from the prism and an apparatus for interpreting the signals received by the cell.

According to the invention, the source illuminates a source slit wich has as its image with respect to an optical system one of the slits of a grille fixed perpendicular to the optical axis and having slits parallel to each other and regularly spaced, each corresponding to an angle of incidence of the optical beam on the prism. Means are provided so that the image of the source slit on the grille can be each of the slits of the grille successively. The pupil, located in the plane of the source, is conjugate with the exit face of the prism and remains stationary when the image of the source slit is moved over the grille.

In a preferred embodiment of the invention, the source slit is fixed and the optical beam falling on the grille is moved parallel to itself by means of a rhombohedron turning about an axis parallel to the optical axis.

According to one characteristic of the invention, the said optical system is constituted by two lenses, the first constituting the pupil and being positioned at the focus of the second.

According to another characteristic of the invention, the source is constituted by an electroluminescent diode, preferably yellow.

An optical fiber will preferably be positioned between the exit of the prism and the measuring cell, and the section of this optical fiber may decrease between the exit face of the prism and the measuring cell.

The apparatus for interpreting the signals received by the cell is constituted by a digital computer.

The invention also concerns the method of measuring the refractive index of a medium, using a refractometer comprising the preceding characteristics.

BRIEF DESCRIPTION OF THE DRAWINGS

The invention will now be described in more detail, with reference more particularly to a particular embodiment of the invention, represented in FIGS. 1 to 3.

DETAILED DESCRIPTION OF AN EMBODIMENT

Figure 1:
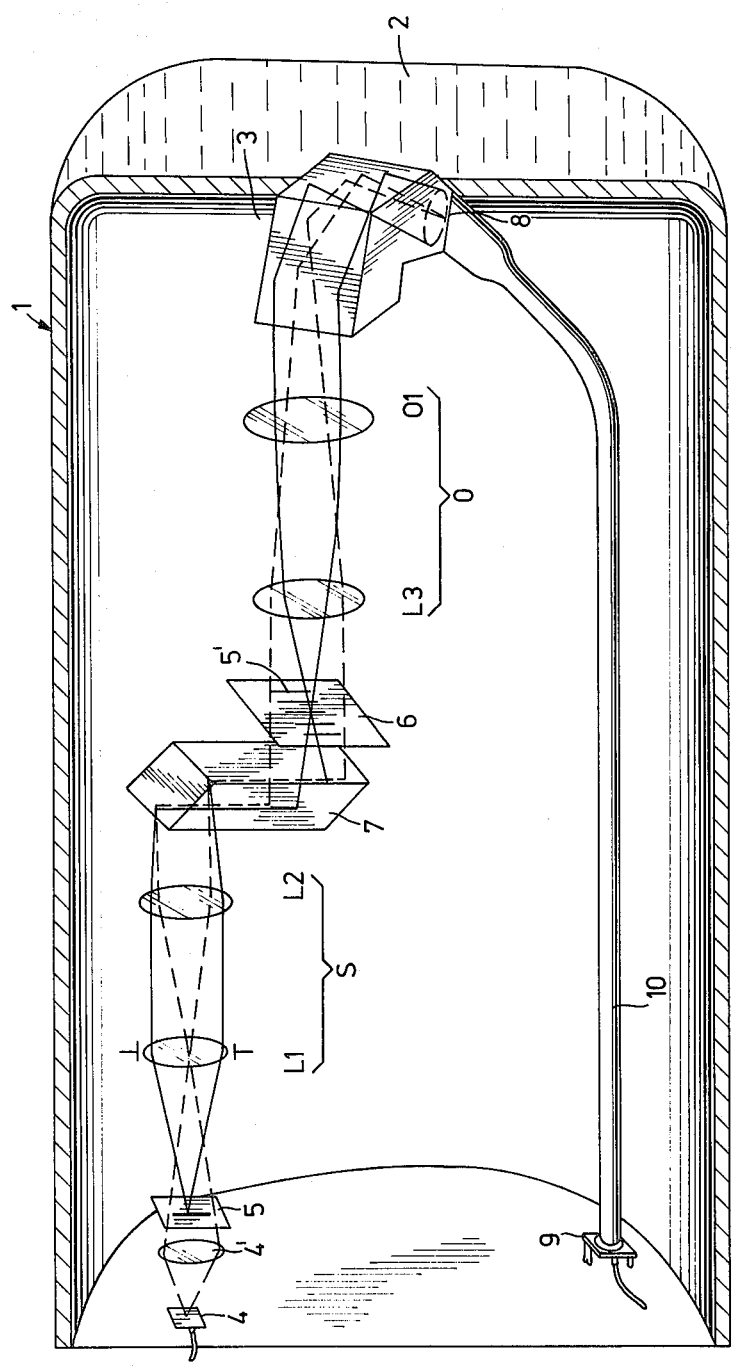
FIG. 1 represents the optical scheme of a refractometer according to the invention.

FIG. 1 represents, positioned in a housing 1, a refractometer for measuring the refractive index of a liquid medium 2. This refractometer includes a reference prism 3 of known index, made of glass, for example, this prism being in direct contact with the medium 2.

A light source 4 illuminates, via a condenser 4', a single source slit 5 positioned in front of it. The source slit 5 has as its image with respect to an optical system S one of the slits 5' of a fixed grille 6 provided with regularly spaced, parallel slits 5'.

Between the optical system S and the grille 6, a rhombohedron 7 is located, capable of turning about an axis parallel to the axis of the pencil from the source slit 5. Thus the rhombohedron 7, by turning relative to itself, allows the image of the source slit 5 to be moved over the grille 6, this image being located successively on each of the slits 5' of the grille 6.

The pencil coming successively from each of the slits 5' corresponds to a defined angle of incidence on the prism 3.

An objective O positioned between the grille and the prism 3 focuses the light rays from the slits 5' of the grille on the prism 3. The objective O has the grille at its focus; the light rays from 5′ therefore fall parallel on the prism 3. The amount of light from the prism 3 can be measured from the exit 8 of the prism. A measuring cell 9 can be positioned immediately at the exit 8 of the prism, but in the embodiment of FIG. 1 the cell 9 has been positioned for preference at the end of an optical fiber 10 connecting the prism 3 to the cell 9, to space the cell 9 from the medium 2 which can be brought to a high temperature. The optical fiber 10 has been represented here with a section which decreases from the prism 3 towards the cell 9. In practice, since the size of the entrance face 8 of the fiber 10 cannot be reduced beyond a certain limit because of a diffraction effect by the slit 5, decreasing the section of the optical fiber 10 allows a cell 9 of small dimensions to be used and therefore improves its performance in noise and at speed.

As the path of the pencil of light from the slit 5 has been represented in continuous lines, a pencil of light from the source 4 has been represented in dotted lines.

It can thus be seen that a lens L1, which constitutes the pupil of the apparatus, has been positioned in the image plane of the source 4 with respect to the condenser 4′. This lens L1, together with the lens L2 at the focus of which it occurs, constitutes the system S. Thus, as the lens L2 throws the lens L1 to infinity, the pupil is stationary when the image 5′ of the slit 5 is moved by the movement of the rhombohedron 7.

The objective O is constituted by a field lens L3, which projects the pupil onto the exit 8 of the prism 3, and by the objective O₁ for focusing rays issued by the slit 5′.

It is therefore established that the image of the source 3 is at the exit 8 of the prism and therefore on the cell 9. This position, for which the source and the cell are conjugate, is that allowing the maximum illuminance on the cell and therefore the use of a low power lamp. The source 4 in particular can be constituted by an electroluminescent diode, which therefore provides a monochromatic source with a long life and emitting a modulated light. A yellow electroluminescent diode can be used, for example, so that known calculations for the sodium line can be used. The apparatus according to the invention therefore allows use of a low power lamp, for example a monochromatic electroluminescent diode making measurement very accurate and having a long life.

Figure 2:
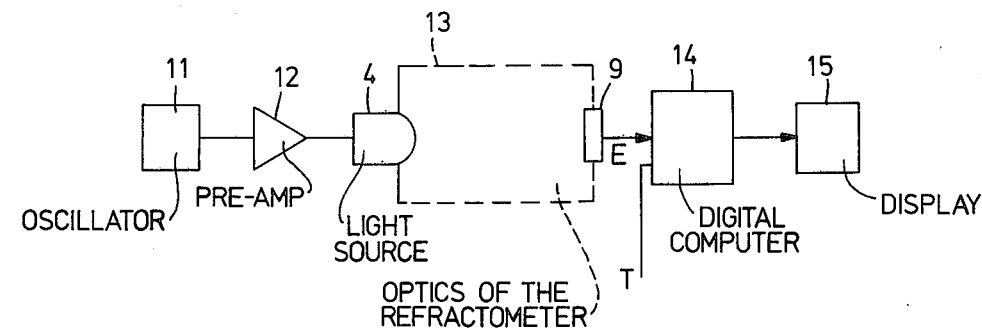
FIG. 2 represents the electronics scheme of the refractometer of FIG. 1.

FIG. 2 shows the electronics scheme of the refractometer according to the invention, which completes the optical scheme.

Figure 3:
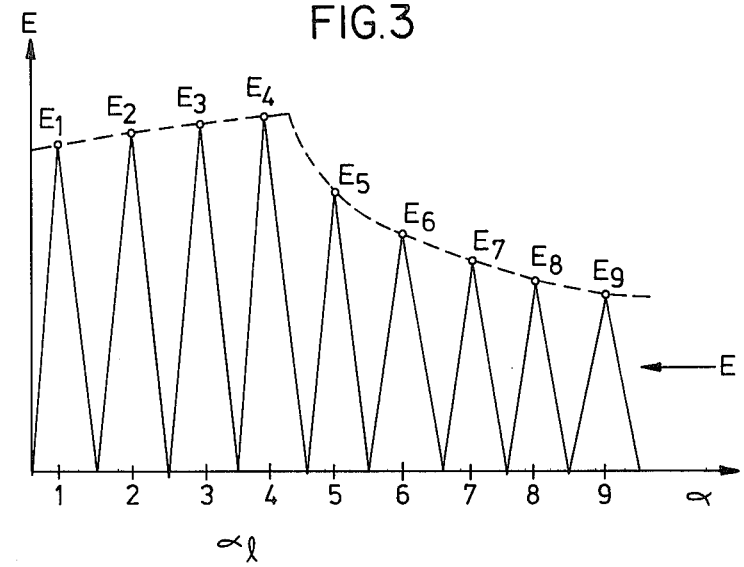
FIG. 3 represents the curve formed by the signals received by the cell.

This scheme comprises an oscillator 11 and a preamp 12 upstream of the electroluminescent diode 4, the reference 4 corresponding to that of FIG. 1. The reference 13 designates the optics of the refractometer as represented in FIG. 1, with the cell 9 at its exit. The signal received by the cell 9, i.e., the illuminance E of this cell, is represented by the curve E of FIG. 3. This signal is digitized at each passage through a maximum: the digital computer 14, positioned downstream of the cell 9, simultaneously receives discrete values $E_1, E_2, \ldots$ of the illuminance and the angle $\alpha$ corresponding to the number of these values (FIG. 3). It selects from these values the one which is nearest the point of discontinuity of the curve of maxima of the curve E. The angle $\alpha_1$, corresponding to the number of the selected value of the illuminance, gives the required limiting angle; the computer 14 immediately deduces the refractive index of the medium 2 from it with the sine law. This index is corrected by the computer 14 as a function of the temperature T of the medium (T has been measured by a suitable sensor and has been entered into the computer 14, as FIG. 2 shows). The index is then displayed at 15 (FIG. 2).

The invention has many advantages. In particular, it allows use of a low power source, for example an electroluminescent diode, which does not have the disadvantages of sources used in conventional refractometers and instead has the advantage of making the apparatus more accurate since the light is monochromatic.

The refractometer according to the invention has been designed not only for the image of the pupil to be on the cell but also for the pupil to be thrown to infinity at the rhombohedron and the grille; this allows the slit to be moved over the grille without affecting the pupil. In addition, an error in the positioning of the rhombohedron does not affect the position of the image of the slit on the grille.

The invention is not limited to the embodiment just described but also covers all embodiments which only differ in detail, variants of execution or by the use of equivalent means.

Thus, the rhombohedron 7 can be omitted and the slit 5 can be moved in a direction perpendicular to the optical axis so that the slit 5 has as its image on the grille 6 each of the slits 5′ successively of the grille 6.

We claim:

1. Refractometer for measuring the refractive index of a medium, using the limiting angle method, comprising
   (a) a reference prism having an exit face and a known refractive index, in contact with the medium to be observed;
   (b) a light source;
   (c) a lens for directing all light rays emanating from said light source onto said prism;
   (d) a photoelectric cell for measuring the image formed at said exit face of said prism;
   (e) an apparatus for interpreting signals received by said cell;
   (f) a grille fixed perpendicular to the optical axis and having a plurality of parallel and regularly spaced slits corresponding to an angle of incidence of an optical beam on said prism;
   (g) said light source illuminating a source slit wich has as its image with respect to an optical system one of said parallel slits in said grille;
   (h) means being provided so that the image of said source slit on said grille can be successively each of said parallel slits of said grille;
   (i) a pupil located in the image plane of said light source and conjugate with said exit face of said prism.

2. Refractometer according to claim 1, wherein said source slit (5) is fixed and the optical beam from said optical system (S) is moved parallel to itself by means of a rhombohedron (7) turning about an axis parallel to said optical axis.

3. Refractometer according to claim 2 or 1, wherein said optical system (S) is constituted by first and second lenses ($L_1$ $L_2$), said first lens ($L_1$), which constitutes the pupil, being positioned at the focus of said second lens ($L_2$).

4. Refractometer according to claim 2 or 1, wherein said light source is constituted by an electroluminescent diode.

5. Refractometer according to claim 2 or 1, including an optical fiber (10) positioned between the exit face (8) of said prism and said measuring cell (9).

6. Refractometer according to claim 5, wherein the section of said optical fiber (10) decreases from the exit face (8) of said prism (3) to said measuring cell (9).

7. Refractometer according to claim 2 or 1, wherein said apparatus for interpreting the signals received by said cell (9) comprises a digital computer (14).

* * * * *